United States Patent [19]

Andrews et al.

[11] 4,096,262
[45] Jun. 20, 1978

[54] POUR-ON ANTHELMINTICS

[75] Inventors: Peter Andrews; Hubert Dorn; Manfred Federmann, all of Wuppertal; Herbert Voege, Leverkusen, all of Germany

[73] Assignee: Bayer Aktiengesellschaft, Leverkusen, Germany

[21] Appl. No.: 783,035

[22] Filed: Mar. 3, 1977

[30] Foreign Application Priority Data

Apr. 6, 1976 Germany .............................. 2614841

[51] Int. Cl.$^2$ ................. A61K 31/495; A61K 31/425; A61K 31/055
[52] U.S. Cl. .................................... 424/250; 424/270; 424/347
[58] Field of Search ....................... 424/270, 347, 250

[56] References Cited

PUBLICATIONS

Schulz et al.–Chem. Abst., vol. 82 (1975) pp. 160, 247j.
Brooker et al.–Chem. Abst., vol. 84 (1976) pp. 184, 905n.

Primary Examiner—Sam Rosen
Attorney, Agent, or Firm—Burgess, Dinklage & Sprung

[57] ABSTRACT

An anthelmintic composition suitable for pour-on application to animals for the treatment of helmintic infections which comprises from 0.5 to 40 parts by weight of an anthelmintic agent which is capable of penetrating the skin of the animal to be treated, 0.5 to 50 parts by weight of one or more spreading oils, 20 to 95 parts by weight of one or more suitable organic or inorganic solvents and 0 to 20 parts by weight of one or more auxiliaries.

36 Claims, No Drawings

POUR-ON ANTHELMINTICS

The present invention relates to pour-on formulations which are suitable for pour-on application to the skin of animals for the treatment of helminthic infections. The pour-on formulations of anthlemintics are known in the art. A pour-on formulation is characterized by an active agent which is dissolved, emulsified or suspended in a suitable solvent or solvent mixture which is well tolerated by the skin of the animal to which it is to be applied either with or without the addition of further auxiliaries. Such a pour-on formulation is applied with the assistance of a suitable device such as a measuring cup or a spray bottle which permits application of the desired amount to the skin of the animal to be treated.

Pour-on formulations and methods of the above type are known in veterinary medicine, such as, for example by Rogoff, W. M., and Kohler, P. H. J., Econ. Ent., 53, 814–817 (1960).

Phosphoric acid esters, such as Ruelen ®, Trichlorphon ® and Fenthion ®, are known to possess insecticidal activity in addition to anthelmintic activity and these compounds are also known to be formulated into pour-on compositions.

However, the anthelmintic activity of Trichlorphon ® and Fenthion ® is only slight and markedly less than is achieved by the oral or subcutaneous administration of said compounds. In the case of Fention ®, it was also found it was possible to achieve significant activity against lungworms (Dictyocaulus) in only some of the cattle treated with pour-on formulations. Ruelen ® has been proposed as a pour-on formulation for treating endoparasitic infections. However, the anthelmintic activity from such pour-on formulations is generally not adequate to combat endoparasitic worms.

Pour-on therapy offers distinct advantages over oral or parenteral administration. When one is dealing with animals, greater ease of handling, the lack of necessity to restrain the animals, minimizing the danger of injury to the animals and to persons giving the treatment, reducing the danger of transmission of diseases by use of injection and minimizing side effects and intolerance to administration of the compound and minimizing expenditures are all important advantages of pour-on therapy.

It is also generally known in the art that higher levels of activity are achieved by oral or parenteral administration rather than by pour-on application (see Herlich et al., Veterinary Medicine, 56, 219–221 (1961) and Hotson, Australian Vet. J., 39, 108–115 (1963)).

It is, however, known in the art that 2,3,5,6-tetrahydro-6-phenylimidazo-(2,1-b)-thiazole, tetramisole, which is also known in the form of its L isomer as levamisole, and acid addition salts thereof may be formulated into pour-on formulations with the use of certain specified solvents and that the activity level is comparable to that achieved on oral or parenteral administration and, in some cases, slightly better. (See German specifications 2,331,793 and 2,408,736 and U.S. Pat. No. 3,980,791.)

It is also known, particularly from the above U.S. patent, that the resorption of the active agent through the skin of the animal varies greatly and is highly dependent on selection of the solvent used. It is also known from said patent that not all solvents may be utilized, either because of the resorption characteristics or because of skin irritation experienced by the animals. The present invention is premised on the surprising discovery that a pour-on formulation may be produced which exhibits good anthelmintic activity which comprises 0.5 to 40 parts by weight of an anthelmintic which is capable of penetrating the skin of the animal to be treated, 0.5 to 50 parts by weight of one or more spreading oils, 20 to 95 parts by weight of one or more organic or inorganic solvents to which the anthelmintic agent is soluble and which is capable of resorption of the active agent through the skin of the animal to be treated in a therapeutically effective amount without damage to the tissues of the animal, and 0 to 20 parts by weight of one or more auxiliaries. Such formulations achieve very good resorption of active agent through the skin of the animal. This is achieved by using one or more spreading oils, as is discussed in more detail below. The use of spreading oils to achieve a wide range of pour-on anthelmintic compositions as defined above is an extremely surprising discovery, particularly in the light of the state of the art which suggests that pour-on formulations having significant anthelmintic activity are difficult to achieve and highly dependent on selection of the solvent.

Spreading oils include those oily liquids which spread particulary well on the skin. Spreading oils are known per se in the cosmetic industry and, as set forth in R. Keymer, Pharm. Ind., 32, 577 (1970), they are characterized, for example, by their surface tension toward air, which should be less than 30 dynes/cm.

The improvement in resorption which is achieved by the use of spreading oils has been described for ointments used in human pharmacy (See W. Ritschel, Angewandte Biopharmazie (Applied Biopharmacy), pages 314–315, Verlag Wissenschaftliche Verlagsgesellschaft mbH, Stuttgart, 1973, edition of Gstirner, F. and Elsner, R.: Arzneimittelforschung, 14, 289 (1964)).

However, the use of such spreading oils in human pharmacy involves different considerations than the present invention which involves the use in formulations for use on animal skin. When used on humans, as a result of spreading, a larger surface area of the skin comes into more intensive contact with the active agent in the ointment formulation. This spreading can be determined experimentally on human skin by the so-called "slap-on" test (See R. Keymer, Pharm. Ind., 32, 577 (1970) or F. Neuwald, K. E. Fetting and A. Szakall, Fette-Seifen-Anstrichmittle, 64, 465 (1962)).

In the case of pour-on formulations, however, for use on animals, it is not possible to demonstrate better dispersion on the surface of the animal's skin due to better spreading on the skin itself since the organic liquids normally used for such formulations such as alcohols, glycol ethers, esters or methylene chloride, already spread very well on the skin of the animal. Thus, the addition of spreading oils to such organic liquids does not produce any greater area of wetted skin surface as is shown by slap-on tests on animals such as cattle.

Additionally, when treating animals, the active agent is in a dissolved form in the pour-on formulation and the solution is miscible with sebaceous matter. Thus an improvement in resorption through the use of a spreading oil is in itself quite unexpected. The substantial improvement in resorption by the addition of a spreading oil according to the present invention thus produced an unexpected and wholly unforeseeable result.

There are three important advantages resulting from the improvement in resorption by the addition of spreading oils:

1. Resorption can be improved with solvents which are well tolerated by the skin of the animal and it is not necessary to employ solvents which, although they give better resorption, on the other hand, are not acceptable from a toxicological point of view for use on animals or are those which give rise to skin irritations;

2. Optimum use can be made of the active agent employed; thus the amount of resorbable active agent which is lost is substantially less than in the case of known pour-on formulations; and 3. It is now possible to use pour-on formulations to treat species of animals in which resorption has hitherto been rendered difficult, such as, pigs, because of the thick fatty layer, and sheep, which have a dense wool coat.

The active agent in the compositions and methods of the present case can be any anthelmintically active agent which is able to penetrate through the skin of the animal to be treated. Representative of exemplary anthelmintically active agents which can be used in the pour-on formulations and methods of the present invention include: compounds of the benzimidazole series such as, for example, 2,3,5,6-tetrahydro-6-phenyl-imidazo(2,1-b)-thiazole (tetramisole or levamisole or the hydrochloride thereof); compounds of the isoquinoline series, such as, for example, 2-(cyclohexanecarbonyl)-4-oxo-1,2,3,6,7,11-b-hexahydro-4H-pyrazino-(2,1-a)-isoquinoline; and Niclofolan ® (5,5'-dichloro-3,3'-dinitro-biphenyl-2,2'-diol). Anthelmintics which are suitable for use in the compositions and methods of the present invention can be easily determined by preliminary screening of their resorption properties when different solvents are used according to routine per se tests.

Anthelmintically active agents of the benzimidazole series and of the isoquinoline series are preferably employed in the form of their free bases.

According to one embodiment of the present invention, the anthelmintic composition comprises 1% to 20% by weight of an anthelmintic agent, 1% to 30% by weight of one or more of said spreading oils, 60% to 90% by weight of one or more of said solvents and 0% to 90% by weight of one or more of said solvents and 0% to 10% by weight of one or more auxiliaries.

According to another embodiment of the present invention, the anthelmintic composition comprises 1% to 30% by weight of one or more of said spreading oils, 60% to 90% by weight of one or more of said solvents and 0% to 10% by weight of one or more of said auxiliaries.

According to another embodiment of the present invention, the anthelmintic agent is tetramisole.

According to another embodiment of the present invention, the anthelmintically active agent is tetramisole or levamisole in the amount of 3% to 30% by weight, and preferably 5% to 20% by weight, a spreading oil is selected from the group consisting of isopropyl myristate, isopropyl palmitate, caprylic/caproic acid triglyceride, saturated triglycerides of natural fatty acids and waxy fatty acid esters which correspond to synthetic duck uropygial gland fat in the amount of 0.5% to 50% by weight and preferably 1% to 30% by weight, and one or more solvents selected from the group consisting of isopropanol, amyl alcohol, methyl ethyl ketone, glycol ethers and methylene chloride in the amount of 20% to 95% by weight and preferably 60% to 90% by weight.

According to another embodiment of the present invention, the anthelmintic agent is levamisole.

According to another embodiment of the present invention, the anthelmintic agent is 2-(cyclohexanecarbonyl)-4-oxo-1,2,3,6,7,11-b-hexahydro-4H-pyrazine-(2,1-a)-isoquinoline.

According to another embodiment of the present invention, the anthelmintic agent is 5,5'-dichloro-3,3'-dinitrobiphenyl-2,2'-diol.

According to another embodiment of the present invention, the anthelmintic composition contains one or more spreading oils, each of which have a surface tension toward air of less than 30 dynes/cm.

Suitable spreading oils for use in the compositions of the present invention include:

Silicone oils of different viscosities,

Fatty acid esters, such as ethyl stearate, di-n-butyl adipate, lauric acid hexyl ester, dipropylene glycol pelargonate, esters of a branched fatty acid of medium chain length with saturated $C_{16}$–$C_{18}$ fatty alcohols, isopropyl myristate, isopropyl palmitate, caprylic/caproic acid esters of saturated fatty alcohols with a chain length of $C_{12}$–$C_{18}$, isopropyl stearate, oleic acid oleyl ester, oleic acid decyl ester, ethyl oleate, lactic acid ethyl ester, waxy fatty acid esters, such as synthetic duck uropygial gland fat, dibutyl phthalate, adipic acid diisopropyl ester, mixtures of esters relating to the latter, and the like, Triglycerides, such as caprylic/caproic acid triglyceride, mixtures of triglycerides with vegetable fatty acids with a chain length of $C_8$–$C_{12}$ or other specially selected natural fatty acids, mixtures of partial glycerides of saturated or unsaturated fatty acids, which may also contain hydroxyl groups, and monodiglycerides of $C_8$/$C_{10}$-fatty acids and others, Fatty alcohols, such as isotridecyl alcohol, 2-octyldodecanol, cetyl stearyl alcohol and oleyl alcohol, and Fatty acids, such as, for example, oleic acid.

Particularly suitable spreading oils include:

isopropyl myristate, isopropyl palmitate, capryl/caproic acid esters of saturated fatty alcohols with a chain length of $C_{12}$–$C_{18}$ and waxy fatty acid esters, such as synthetic duck uropygial gland fat.

All organic and inorganic solvents which dissolve an anthelmintically active agent in an adequate concentration and which are capable of achieving adequate resorption of the active agent through the skin of the animal to be treated without damage to the tissues can be used as solvents in the compositions and methods of the present invention. Suitable solvents include:

Alkanols, such as ethyl alcohol, isopropyl alcohols, n-butyl alcohol, amyl alcohol and octanol, Glycols, such as propylene glycol, 1,3-butylene glycol, ethylglycol and dipropylene glycol monomethyl ether, Aromatic alcohols, such as benzyl alcohol, Carboxylic acid esters, such as, for example, ethyl acetate, benzyl benzoate and butyl acetate, Aromatic and/or aliphatic hydrocarbons, including halogenated derivatives thereof, Oils which do not fall under the definition of spreading oils: such as, for example, cottonseed oil, groundnut oil, maize kernel oil, olive oil, castor oil and sesame oil, Water and Ketones, such as, for example, acetone and methyl ethyl ketone.

Furthermore, inter alia, compounds such as dimethylsulphoxide, dimethylacetamide, dimethylformamide, N-methylpyrrolidone, dioxane and 2-dimethyl-4-hydroxymethyl-1,3-dioxalane are very suitable as solvents.

Lower alcohols with up to 8 carbon atoms in the molecule and lower ketones, such as, for example, acetone and methyl ethyl ketone, and lower halogenated hydrocarbons, such as, for example, methylene chloride, are particularly suitable.

One or more of the solvents described above can be employed for the preparation of the pour-on formulations according to the present invention.

As described above, the compositions and methods of the present invention may include one or more auxiliaries. Such auxiliaries include:

(a.) Adhesion promoters, for example carboxymethylcellulose, methylcellulose and other cellulose derivatives and starch derivatives, polyacrylates, alginates, gelatine, gum arabic, polyvinylpyrrolidone, polyvinyl alcohol, copolymers of methyl vinyl ether and maleic anhydride, polyethylene glycols, paraffins, oils, waxes, colloidal silica or mixtures of the substances listed.

(b.) Surface-active agents (comprising emulsifiers and wetting agents), for example 1. anionic surface-active agents, such as Na lauryl-sulphate, fatty alcohol ether-sulphates and the monoethanolamine salt of mono-/di-alkyl-polyglycol ether orthophosphoric acid esters, 2. cationic surface-active agents, such as cetyltrimethyl-ammonium chloride, 3. ampholytic surface-active agents, such as di-Na N-lauryl-β-iminodipropionate or lecithin and 4. non-ionic surface-active agents, for example polyoxethylated castor oil, polyoxyethylated sorbitan monooleate, sorbitane monostearate, ethyl alcohol, glycerol monostearate, polyoxyethylene stearate and alkylphenol polyglycol ethers, and (c.) stabilizers in order to prevent the chemical decomposition which occurs in the case of some anthelmintic active compounds, such as, for example, antioxidants, for example tocopherols and butyl hydroxyanisole.

The compositions of the present invention may be made up before use in unit dosage form. This means that the composition is made up into physically discrete coherent portions suitable for pour-on administration and that each portion contains a daily dose of the active ingredient or a multiple thereof of up to about four times the daily dose. Alternatively, the composition may be made up into a physically discrete portion containing a sub-multiple of a daily dose, down to about a fortieth of the daily dose. Whether the unit dosage form contains a daily dose or a half, a third or a quarter of said daily dosage will depend upon whether the composition is to be administered once, twice, three times or four times a day respectively. Typical examples of unit dosage forms are sealed vials each containing a daily dose of the composition and which may be opened immediately before use and poured onto the animal's back. By this procedure, one can avoid having to measure out each dose of the composition to be administered at the situs and immediately before administration.

Preferred types of pour-on formulations include solutions, suspensions, emulsions and sprays.

The pour-on formulations according to the invention are prepared by dissolving, emulsifying or suspending the anthelmintically active agent in a suitable solvent or solvent mixture which is tolerated by the skin, adding the spreading oil and optionally adding the further auxiliaries.

The above sequence of process steps is not critical; it can be changed or the constituents of the pour-on formulation according to the invention can also optionally be added together simultaneously, while stirring continuously. For the preparation, the individual constituents were added in the quantity ratios indicated above.

The formulations according to the invention which are listed in the text which follows were prepared as indicated above and in each case were tested, in respect of the blood level values, in comparison with formulations which contained no spreading oils. These blood level values, which represent a direct criterion for the particular pour-on formulation, were determined as follows.

Pour on formulations representative of the present invention were prepared and tested to determine the blood levels of anthelmintically active agents as compared to pour-on formulations which did not contain spreading oils.

Method

The active compound is isolated from the blood by the method of HOLBROCK & SCALES (Analyt. Biochem. 18, 46–53 (1957)). The quantitative determination is carried out by spectrophotometry by measuring the extinction at a wavelength of 215 mm.

Using the pour-on method it is possible to obtain blood levels which are equal to or higher than those obtained after peroral and subcutaneous administration. Subcutaneous administration gives higher blood levels than the pour-on method only 2 hours after treatment.

The blood level method is a possibility for testing the resorption of the active compound in the case of the pour-on formulation at a cost which is low compared with that of the worm test. The blood level in cattle was determined after treatment with 20 mg of active compound/kg of body weight.

The blood level values are given in $\mu g$ of active compound/ml of blood.

EXAMPLES A TO C

The following solutions of Levamisole base are prepared by mixing

| Example | A | B | C |
|---|---|---|---|
| Levamisole base | 10.0 g | 10.0 g | 10.0 g |
| liquid paraffin of high viscosity | — | 10.0 g | — |
| isopropyl myristate | — | — | 10.0 g |
| isopropanol | to make up to 100 ml | to make up to 100 ml | to make up to 100 ml |

In the case of each formulation, 3 cattle were each treated with 20 mg/kg by the pour-on method and the blood levels were determined after 2, 4 and 6 hours. The average values can be seen in the table which follows:

| Blood level in $\mu g$/ml after | | hours | |
|---|---|---|---|
| | 2 | 4 | 6 |
| Formulation of Example A | 0.9 | 0.7 | 0.5 |
| B | 1.1 | 0.75 | 0.40 |
| C | 2.5 | 1.5 | 0.7 |

It can be seen from this table that the addition of liquid paraffin, which is not a spreading oil, has no influence on the penetration through the skin but, on the other hand, the addition of isopropyl myristate, which, as is known, spreads well, approximately doubles the resorption.

EXAMPLES D TO F

Solutions of Levamisole base which contain different amounts of isopropyl myristate are prepared:

| Formulation of Example | A | D | E | C | F |
|---|---|---|---|---|---|
| Levamisol base | 10.0 g | 10.0 g | 10.0 g | 10.0 g | 10.0 g |
| isopropyl myristate | — | 1.0 g | 5.0 g | 10.0 g | 30.0 g |
| isopropanol | to make up to 100 ml | to make up to 100 ml | to make up to 100 ml | to make up to 100 ml | to make up to 100 ml |

The blood levels of three cattle in each case were again determined after pour-on application, analogously to Examples A to C.

The formulations of Examples A and C have been taken to enable the influence of the concentration of the spreading oil to be better shown.

| Blood level in μg/ml after | | 2 hours | 4 | 6 |
|---|---|---|---|---|
| Formulation of Example | A | 0.9 | 0.7 | 0.5 |
| | D | 1.2 | 0.9 | 0.8 |
| | E | 2.0 | 1.5 | 0.7 |
| | C | 2.5 | 1.5 | 0.7 |
| | F | 3.3 | 2.8 | 1.6 |

EXAMPLES G AND H

Two further spreading oils were employed in place of isopropyl myristate. In the table they are compared with the isopropanol formulation.

| Example | A | G | H |
|---|---|---|---|
| Levamisole base | 10.0 g | 10.0 g | 10.0 g |
| isopropyl palmitate | — | 3.0 g | — |
| caprylic/caproic acid triglyceride | — | — | 10.0 g |
| isopropanol | to make up to 100 ml | to make up to 100 ml | to make up to 100 ml |

The comparisons of the blood levels of Levamisole — determined analogously to the other examples — can be seen from the table which follows:

| Blood level in ug/ml after | | 2 hours | 4 | 6 |
|---|---|---|---|---|
| Formulation of Example | A | 0.9 | 0.7 | 0.5 |
| | G | 1.4 | 1.1 | 0.7 |
| | H | 2.6 | 1.5 | 0.8 |

EXAMPLES I AND K

The following formulations were prepared and the blood levels were determined as indicated for the other examples:

| Example | I | K |
|---|---|---|
| Levamisole base | 10.0 g | 10.0 g |
| isopropyl myristate | — | 35.85 g |
| methyl ethyl ketone | to make up to 100 ml | to make up to 100 ml |

| Blood level in ug/ml after | 2 hours | 4 | 6 |
|---|---|---|---|
| Formulation I | 0.70 | 0.6 | 0.4 |
| Formulation K | 1.2 | 1.1 | 0.7 |

EXAMPLES L TO N

| Example | L | M | N |
|---|---|---|---|
| Levamisole base | 10.0 g | 10.0 g | 10.0 g |
| methylene chloride | 20.0 g | 20.0 g | 20.0 g |
| polyoxyethylated castor oil | 7.5 g | 7.5 g | 7.5 g |
| isopropyl myristate | to make up to 100 ml | | |
| sunflower oil | | to make up to 100 ml | |
| liquid paraffin of low viscosity | | | to make up to 100 ml |

These solutions must be shaken before use, so that a thin emulsion is employed.

| Blood level in ug/ml after | | 2 hours | 4 | 6 |
|---|---|---|---|---|
| Formulation of Example | L | 2.10 | 1.90 | 1.5 |
| | M | 0.5 | 0.9 | 1.0 |
| | N | 0.6 | 0.8 | 0.8 |

EXAMPLES O TO Q

In a parallel test, two spreading agent formulations were tested — analogously to the above examples — in comparison with a paraffin formulation.

| Example | O | P | Q |
|---|---|---|---|
| Levamisole base | 10.0 g | 10.0 g | 10.0 g |
| paraffin of low viscosity | 10.0 g | — | — |
| Softisan 378 ® ( = mixture of saturated triglycerides of selected natural fatty acids) | — | 20.0 g | — |
| waxy branched fatty acid esters which correspond to synthetic duck uropygial gland fat | — | — | 10.0 g |
| isopropanol | to make up to 100 ml | to make up to 100 ml | to make up to 100 ml |

| Blood level in ug/ml after | | 2 hours | 4 | 6 |
|---|---|---|---|---|
| Formulation of Example | P | 0.95 | 1.12 | 0.81 |

-continued

| Blood level in ug/ml after | | hours | | |
|---|---|---|---|---|
| | | 2 | 4 | 6 |
| | Q | 1.10 | 1.48 | 1.03 |

EXAMPLES R TO T

In a parallel test, different amounts of isopropyl myristate were tested in dipropylene glycol monomethyl ether. The addition of the spreading oil has a distinct penetration-promoting effect in this solvent also.

| Examples | R | S | T |
|---|---|---|---|
| Levamisole base | 10.0 | 10.0 | 10.0 |
| isopropyl myristate | — | 5.0 | 10.0 |
| dipropylene glycol monomethyl ether | to make up to 100.0 | to make up to 100.0 | to make up to 100.0 |

| Blood level in ug/ml after | | hours | | |
|---|---|---|---|---|
| | | 2 | 4 | 6 |
| Formulation of Example | R | 0.56 | 0.86 | 0.90 |
| | S | 1.55 | 1.39 | 1.12 |
| | T | 3.16 | 3.01 | 2.11 |

What is claimed is:

1. An anthelmintic composition suitable for pour-on application to animals for the treatment of helminthic infections which comprises 5 to 20 percent by weight of an anthelmintic agent which is capable of penetrating the skin of the animal to be treated, 1 to 30 percent by weight of one or more spreading oils, selected from the group consisting of isopropyl myristate isopropyl palmitate, caprylic/caproic acid triglyceride, saturated triglycerides of natural fatty acids and waxy fatty acid esters which correspond to synthetic duck uropygial gland fat and 60 to 90 percent by weight of one or more solvents selected from the group consisting of isopropanol, amyl alcohol, methyl ethyl ketone, glycol ethers and methylene chloride, and 0 to 10 percent by weight of one or more auxiliaries.

2. A composition according to claim 1 wherein the anthelmintic agent is a compound of the benzimidazole or isoquinoline series.

3. A composition according to claim 1 wherein the anthelmintic agent is tetramisole.

4. A composition according to claim 1 wherein the anthelmintic agent is levamisole.

5. A composition according to claim 1 wherein the anthelmintic agent is 2-(cyclohexanecarbonyl)-4-oxo-1,2,3,6,7,11-b-hexahydro-4H-pyrazino-(2,1-a)-isoquinoline.

6. A composition according to claim 1 wherein the anthelmintic agent is 5,5'-dichloro-3,3'-dinitrobiphenyl-2,2'-diol.

7. A composition according to claim 1 which comprises levamisole base and isopropyl myristate in equal proportions by weight and isopropanol in an amount sufficient to make up a 100 ml. unit dosage.

8. A composition according to claim 1 which comprises levamisole base and isopropyl myristate in a weight ratio of 10:1 and isopropanol in an amount sufficient to make up a 100 ml. unit dosage.

9. A composition according to claim 1 which comprises levamisole base and isopropyl myristate in a weight ratio of 2:1 and isopropanol in an amount sufficient to make up a 100 ml. unit dosage.

10. A composition according to claim 1 which comprises levamisole base and isopropyl myristate in a weight ratio of 1:3 and isopropanol in an amount sufficient to make up a 100 ml. unit dosage.

11. A composition according to claim 1 which comprises levamisole base and isopropyl palmitate in a weight ratio of 10:3 and isopropanol in an amount sufficient to make up a 100 ml. unit dosage.

12. A composition according to claim 1 which comprises levamisole base and caprylic/caproic acid triglyceride in equal proportions by weight and isopropanol in an amount sufficient to make up a 100 ml. unit dosage.

13. A composition according to claim 1 which comprises levamisole base and isopropyl myristate in a weight ratio of 1:3.6 and methyl ethyl ketone in an amount sufficient to make up a 100 ml. unit dosage.

14. A composition according to claim 1 which comprises levamisole base, methylene chloride and polyoxyethylated castor oil in a weight ratio of 1:2:0.75 and isopropyl myristate in an amount sufficient to make up a 100 ml. unit dosage.

15. A composition according to claim 1 which comprises levamisole base and Softisan ® in a weight ratio of 1:2 and isopropanol in an amount sufficient to make up a 100 ml. unit dosage.

16. A composition according to claim 1 which comprises levamisole base and waxy branched fatty acid esters which correspond to synthetic duck uropygial gland fat in equal proportions by weight and isopropanol in an amount sufficient to make up a 100 ml. unit dosage.

17. A composition according to claim 1 which comprises levamisole base and isopropyl myristate in a weight ratio of 2:1 and dipropylene glycol monomethyl ether in an amount sufficient to make up a 100 ml. unit dosage.

18. A composition according to claim 1 which comprises levamisole base and isopropyl myristate in equal proportions by weight and dipropylene glycol monomethyl ether in an amount sufficient to make up a 100 ml. unit dosage.

19. A method of treating helminthic infections in animals which comprises pouring onto the skin of the animal to be treated an anthelmintically effective amount of a composition which comprises 5 to 20 percent by weight of an anthelmintic agent which is capable of penetrating the skin of the animal to be treated, 1 to 30 percent by weight of one or more spreading oils, selected from the group consisting of isopropyl myristate isopropyl palmitate, caprylic/caproic acid triglyceride, saturated triglycerides of natural fatty acids and waxy fatty acid esters which correspond to synthetic duck uropygial gland fat and 60 to 90 percent by weight of one or more solvents selected from the group consisting of isopropanol, amyl alcohol, methyl ethyl ketone, glycol ethers and methylene chloride, and 0 to 10 percent by weight of one or more auxiliaries.

20. A method according to claim 19 wherein the anthelmintic agent is a compound of the benzimidazole or isoquinoline series.

21. A method according to claim 19 wherein the anthelmintic agent is tetramisole.

22. A method according to claim 19 wherein the anthelmintic agent is levamisole.

23. A method according to claim 19 wherein the anthelmintic agent is 2-(cyclohexanecarbonyl)-4-oxo-1,2,3,6,7,11-b-hexahydro-4H-pyrazino-(2,1-a)-isoquinoline.

24. A method according to claim 19 wherein the anthelmintic agent is 5,5'-dichloro-3,3'-dinitrobiphenyl-2,2'-diol.

25. A method according to claim 19 wherein the composition comprises levamisole base and isopropyl myristate in equal proportions by weight and isopropanol in an amount sufficient to make up a 100 ml. unit dosage.

26. A method according to claim 19 wherein the composition comprises levamisol base and isopropyl myristate in a weight ratio of 10:1 and isopropanol in an amount sufficient to make up a 100 ml. unit dosage.

27. A method according to claim 19 wherein the composition comprises levamisole base and isopropyl myristate in a weight ratio of 2:1 and isopropanol in an amount sufficient to make up a 100 ml. unit dosage.

28. A method according to claim 19 wherein the composition comprises levamisole base and isopropyl myristate in a weight ratio of 1:3 and isopropanol in an amount sufficient to make up a 100 ml. unit dosage.

29. A method according to claim 19 wherein the composition comprises levamisole base and isopropyl palmitate in a weight ratio of 10:3 and isopropanol in an amount sufficient to make up a 100 ml. unit dosage.

30. A method according to claim 19 wherein the composition comprises levamisole base and caprylic-/caproic acid triglyceride in equal proportions by weight and isopropanol in an amount sufficient to make up a 100 ml. unit dosage.

31. A method according to claim 19 wherein the composition comprises levamisole base and isopropyl myristate in a weight ratio of 1:3.6 and methyl ethyl ketone in an amount sufficient to make up a 100 ml. unit dosage.

32. A method according to claim 19 wherein the composition comprises levamisole base, methylene chloride and polyoxyethylated castor oil in a weight ratio of 1:2:0.75 and isopropyl myristate in an amount sufficient to make up a 100 ml. unit dosage.

33. A method according to claim 19 wherein the composition comprises levamisole base and Softisan ® in a weight ratio of 1:2 and isopropanol in an amount sufficient to make up a 100 ml. unit dosage.

34. A method according to claim 19 wherein the composition comprises levamisole base and waxy branched fatty acid esters which correspond to synthetic duck uropygial gland fat in equal proportions by weight and isopropanol in an amount sufficient to make up a 100 ml. unit dosage.

35. A method according to claim 19 wherein the composition comprises levamisole base and isopropyl myristate in a weight ratio of 2:1 and dipropylene glycole monomethyl ether in an amount sufficient to make up a 100 ml. unit dosage.

36. A method according to claim 19 wherein the composition comprises levamisole base and isopropyl myristate in equal proportions by weight and dipropylene glycol monomethyl ether in an amount sufficient to make up a 100 ml. unit dosage.

* * * * *

UNITED STATES PATENT AND TRADEMARK OFFICE
CERTIFICATE OF CORRECTION

PATENT NO. : 4,096,262

DATED : June 20, 1978

INVENTOR(S) : Peter Andrews, et al.

It is certified that error appears in the above-identified patent and that said Letters Patent are hereby corrected as shown below:

On Title Page, filing date is incorrect.

" March 3, 1977" should read --March 30, 1977--.

Signed and Sealed this

Twenty-sixth Day of December 1978

[SEAL]

Attest:

RUTH C. MASON
*Attesting Officer*

DONALD W. BANNER
*Commissioner of Patents and Trademarks*